US00PP35792P2

(12) United States Plant Patent
Mathey

(10) Patent No.: US PP35,792 P2
(45) Date of Patent: May 7, 2024

(54) ***DIERVILLA* PLANT NAMED 'SMNDSD'**

(50) Latin Name: ***Diervilla* x *splendens***
Varietal Denomination: SMNDSD

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,861

(22) Filed: Aug. 30, 2023

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Diervilla* plant named 'SMNDSD', characterized by its upright to outwardly spreading and mounding plant habit; vigorous growth habit and rapid growth rate; freely branching habit; dense and bushy appearance; reddish brown-colored stems; leaves that are bronze orange in color slightly tinged with yellow green in the spring and become yellow green in color tinged with bronze orange during the summer and autumn; numerous soft butter yellowish green-colored flowers; and good garden performance.

3 Drawing Sheets

Figure 1:
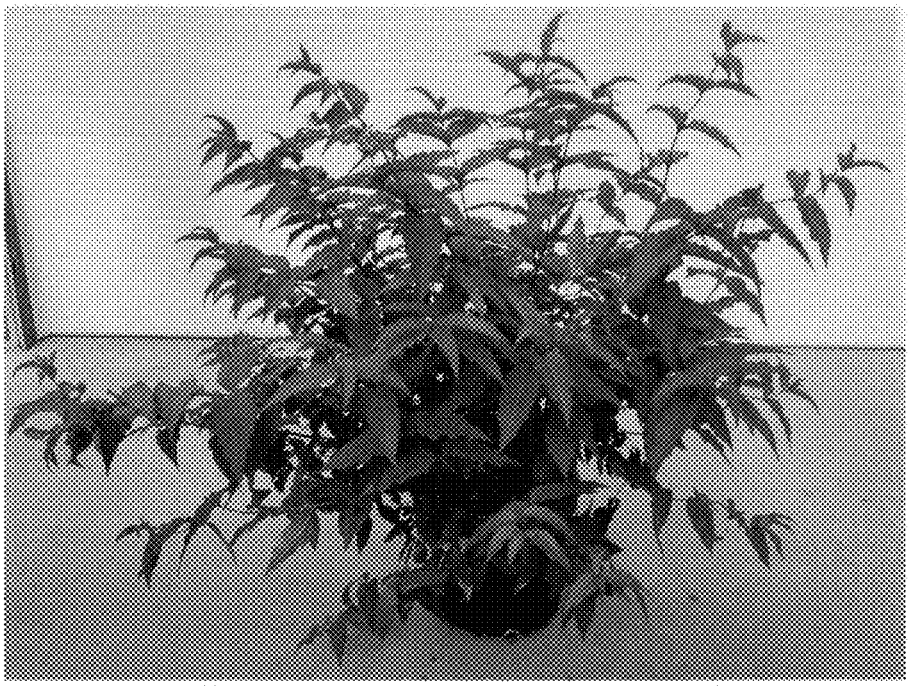

Botanical designation: *Diervilla* x *splendens*.
Cultivar denomination: 'SMNDSD'.

BACKGROUND OF THE INVENTION

The present invention relates to a new and distinct cultivar of *Diervilla* plant, botanically known as *Diervilla* x *splendens*, commonly referred to as Bush Honeysuckle and hereinafter referred to by the cultivar name 'SMNDSD'.

The new *Diervilla* is a product of a planned breeding program conducted by the Inventor in Grand Haven, Michigan. The objective of the breeding program was to develop new freely branching *Diervilla* plants with attractive and vibrant leaf coloration.

The new *Diervilla* plant originated from an open-pollination in 2020 on Grand Haven, Michigan of *Diervilla* x *splendens* 'El Madrigal', disclosed in U.S. Plant Pat. No. 28,060, as the female, or seed, parent with an unknown selection of *Diervilla* x *splendens* as the male, or pollen, parent. The new *Diervilla* plant was discovered and selected by the Inventor in 2021 as a single flowering plant within the progeny of the stated open-pollination in a controlled environment in Grand Haven, Michigan.

Asexual reproduction of the new *Diervilla* plant by softwood stem cuttings in a controlled greenhouse environment in Grand Haven, Michigan since 2021 has shown that the unique features of this new *Diervilla* plant are stable and reproduced true to type in successive generations of asexual reproduction.

SUMMARY OF THE INVENTION

Plants of the new *Diervilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNDSD'. These characteristics in combination distinguish 'SMNDSD' as a new and distinct *Diervilla* plant:

1. Upright to outwardly spreading and mounding plant habit.
2. Vigorous growth habit and rapid growth rate.
3. Freely branching habit; dense and bushy appearance.
4. Reddish brown-colored stems.
5. Leaves that are bronze orange in color slightly tinged with yellow green in the spring and become yellow green in color tinged with bronze orange during the summer and autumn.
6. Numerous soft butter yellowish green-colored flowers.
7. Good garden performance.

Plants of the new *Diervilla* can be compared to plants of the female parent, 'El Madrigal'. In side-by-side comparisons, plants of the new *Diervilla* differ primarily from plants of 'El Madrigal' in leaf color as leaves of the new *Diervilla* are bronze orange in color slightly tinged with yellow green in the spring and become yellow green in color tinged with bronze orange during the summer and autumn whereas leaves of plants of 'El Madrigal' are yellow in color in the spring and become burgundy to greenish brown in color in the summer and autumn.

Plants of the new *Diervilla* can also be compared to plants of *Diervilla* x *splendens* 'G2X885411', disclosed in U.S. Plant Pat. No. 28,403. In side-by-side comparisons, plants of the new *Diervilla* differ primarily from plants of 'G2X885411' in leaf color as leaves of the new *Diervilla* are bronze orange in color slightly tinged with yellow green in the spring and become yellow green in color tinged with bronze orange during the summer and autumn whereas leaves of plants of 'G2X885411' are green in color lightly tinged with orange in the spring becoming burgundy in the summer and red in the autumn. In addition, plants of the new *Diervilla* are denser and more mounded than and not as open in plant habit as plants of 'G2X885411'.

BRIEF DESCRIPTION OF THE PHOTOGRAPHS

The accompanying colored photographs illustrate the overall appearance of the new *Diervilla* plant showing the colors as true as it is reasonably possible to obtain in colored reproductions of this type. Colors in the photographs may differ slightly from the color values cited in the detailed botanical description which accurately describe the colors of the new *Diervilla* plant.

The photograph on the first sheet (FIG. 1) is a side perspective view of a typical plant of 'SMNDSD' grown during the summer.

Figure 2:
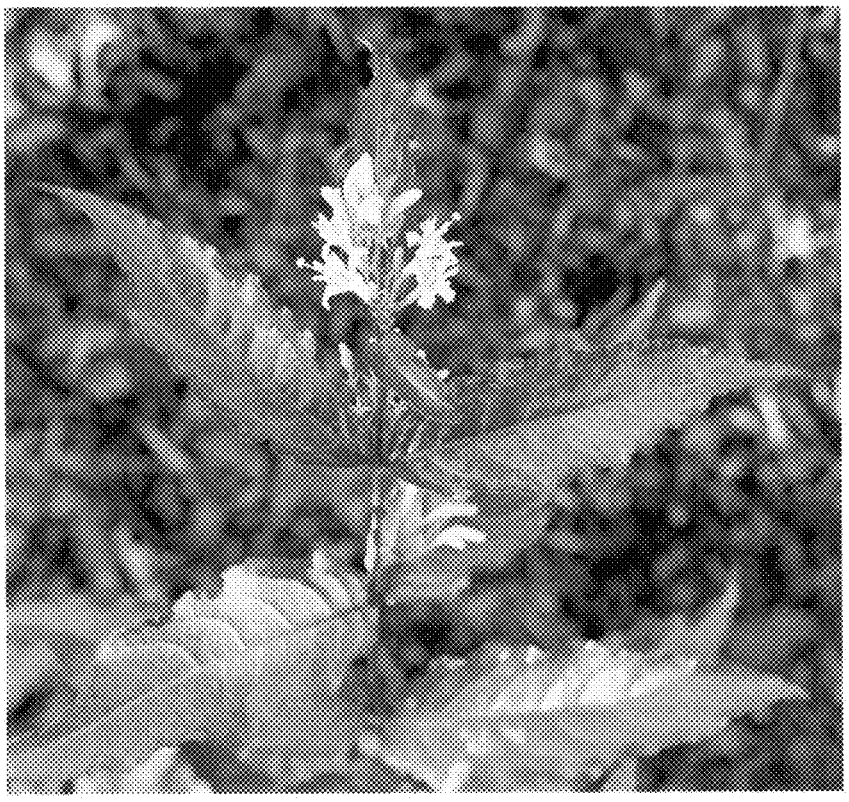

The photograph on the second sheet (FIG. 2) is a close-up view of a typical flowering stem of 'SMNDSD'.

Figure 3:
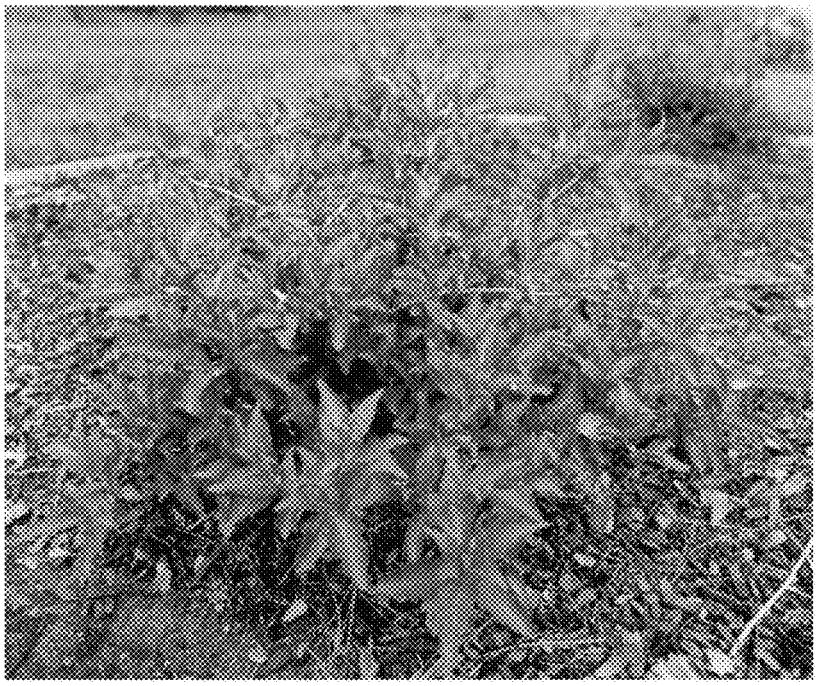

The photograph on the third sheet (FIG. 3) is side perspective view of a typical flowering plant of 'SMNDSD' grown during the spring.

DETAILED BOTANICAL DESCRIPTION

The aforementioned photographs and following observations, measurements and values describe plants grown in the spring and summer in three-gallon containers in a polyethylene-covered greenhouse in Grand Haven, Michigan and under cultural practices typical of commercial *Diervilla* production. During the production of the plants, day temperatures ranged from 18 C to 27 C and night temperatures ranged from 5 C to 10 C. Plants were two years old when the photographs and the description were taken. In the description, color references are made to The Royal Horticultural Society Colour Chart, 2015 Edition, except where general terms of ordinary dictionary significance are used.

Botanical classification: *Diervilla* x *splendens* 'SMNDSD'.

Parentage:

- *Female, or seed, parent.*—*Diervilla* x *splendens* 'El Madrigal', disclosed in U.S. Plant Pat. No. 28,060.
- *Male, or pollen, parent.*—Unknown selection of *Diervilla* x *splendens*, not patented.

Propagation:

- *Type.*—By softwood stem cuttings.
- *Time to initiate roots, summer.*—About 10 to 21 days at temperatures about 18 C to 27 C.
- *Time to produce a rooted young plant, summer.*—About four weeks at temperatures about 18 C to 27 C.
- *Root description.*—Medium in thickness to thick; fleshy to fibrous; typically white to tan in color, actual color of the roots is dependent on substrate composition, water quality, fertilizer, substrate temperature and physiological age of roots.
- *Rooting habit.*—Moderately freely branching; medium density.

Plant description:

- *Plant form and growth habit.*—Perennial deciduous shrub; upright and outwardly spreading and mounding plant habit; vigorous growth habit and rapid growth rate.
- *Branching habit.*—Freely branching habit; about 30 to 40 lateral branches develop per plant; pinching enhances lateral branch development.
- *Plant height.*—About 70 cm.
- *Plant diameter* (*area of spread*).—About 110 cm.

Lateral branch description:

- *Length.*—About 60 cm to 70 cm.
- *Diameter.*—About 6 mm.
- *Internode length.*—About 4 cm.
- *Aspect.*—About 15 to 60 degrees from vertical.
- *Strength.*—Moderately strong; somewhat flexible.
- *Texture.*—Slightly pubescent on youngest stems; with subsequent development, mostly smooth, glabrous; longitudinally ridged.
- *Color, developing, upper and lower surfaces.*—Close to 174A.
- *Color, developed, upper and lower surfaces.*—Close to 199A to 199B.

Leaf description:

- *Arrangement.*—Opposite, simple.
- *Length.*—About 11.4 cm.
- *Width.*—About 4.7 cm.
- *Shape.*—Elliptic.
- *Apex.*—Acuminate.
- *Base.*—Obtuse.
- *Margin.*—Serrulate.
- *Texture, upper surface.*—Smooth, glabrous.
- *Texture, lower surface.*—Smooth, glabrous with prominent midrib.
- *Venation pattern.*—Pinnate.
- *Color.*—Developing leaves, during spring, upper and lower surfaces: Close to 166A variably tinged with close to 144A. Fully expanded leaves, during the summer and autumn, upper surface: Close to 144A variably tinged with close to 166A to 166B; venation, close to 174A. Fully expanded leaves, during the summer and autumn, lower surface: Close to 144A variably tinged with close to 166A to 166B; venation, close to 174B.
- *Petioles.*—Length: About 3 mm. Diameter: About 2 mm. Texture, upper and lower surfaces: Smooth, glabrous. Color, upper surface: Close 174A. Color, lower surface: Close to 174B.

Flower description:

- *Flower appearance and arrangement.*—Salverform flowers arranged in terminal cymes; freely flowering habit with about 30 to 40 flowers per inflorescence with numerous inflorescences developing per plant; flowers face upright to outwardly.
- *Fragrance.*—None detected.
- *Natural flowering season.*—Plants flower continuously during the early to mid-summer in Michigan; flowers not persistent.
- *Inflorescence diameter.*—About 3.5 cm.
- *Inflorescence height.*—About 3 cm.
- *Flower diameter.*—About 7 mm.
- *Flower length.*—About 1.5 cm.
- *Flower throat diameter* (*at base of petal lobes*).—About 5 mm.
- *Flower tube length.*—About 1 cm.
- *Flower tube diameter* (*at base of tube*).—About 2 mm.
- *Flower buds.*—Length: About 5 mm to 10 mm. Diameter: About 2 mm. Shape: Oblong. Color: Close to 145A.
- *Petals.*—Quantity and arrangement: Five fused with apices free. Length: About 6 mm. Width: About 2 mm. Shape: Oblong. Apex: Obtuse to rounded. Margin: Entire. Texture, upper and lower surfaces: Smooth, silky; glabrous. Color: When opening and fully opened, upper surface: Close to 150C to 150D;

flower throat, close to 150C to 150D. When opening and fully opened, lower surface: Close to 150C to 150D; flower tube, close to 150C to 150D.

*Sepals*.—Quantity and arrangement: Five in a single whorl fused at the base; cup-shaped calyx. Length: About 3 mm. Width: About 0.5 mm to 1 mm. Shape: Acicular, fine. Apex: Acute. Margin: Entire. Texture, upper and lower surfaces: Smooth, glabrous. Color, upper and lower surfaces: Close to 144B.

*Peduncles*.—Length: About 1.5 cm. Diameter: About 1 mm. Aspect: About 45 to 90 degrees from vertical. Strength: Strong. Texture: Smooth, glabrous. Color, upper and lower surfaces: Close to 144B.

*Pedicels*.—Length: About 8 mm. Diameter: About 1 mm. Aspect: About 45 degrees from peduncle axis. Strength: Strong. Texture: Smooth, glabrous. Color, upper and lower surfaces: Close to 144B variably tinged with close to 176A.

*Reproductive organs*.—Stamens: Quantity per flower: Five. Filament length: About 1 cm. Filament color: Close to 151D. Anther length: About 4 mm. Anther shape: Linear. Anther color: Close to 160A. Pollen amount: Scarce. Pollen color: Close to 160A. Pistils: Quantity per flower: One. Pistil length: About 1.5 cm. Stigma shape: Round. Stigma color: Close to 146B. Style length: About 1.25 cm. Style color: Close to 151D.

*Fruits and seeds*.—To date, fruit and seed development have not been observed on plants of the new *Diervilla*.

Garden performance: Plants of the new *Diervilla* have been observed to have good garden performance and tolerate temperatures ranging from −31 C to 38 C.

Pathogen & pest resistance: To date, plants of the new *Diervilla* have not been shown to be resistant to pathogens and pests common to *Diervilla* plants.

It is claimed:

1. A new and distinct *Diervilla* plant named 'SMNDSD' as illustrated and described.

* * * * *